United States Patent
Hadjioannou et al.

(10) Patent No.: US 9,510,783 B2
(45) Date of Patent: Dec. 6, 2016

(54) SYSTEM FOR VASCULAR ACCESS IN LABORATORY ANIMALS

(71) Applicant: THE REGENTS OF THE UNIVERSITY OF CALIFORNIA, Oakland, CA (US)

(72) Inventors: Arion-Xenofon F. Hadjioannou, Los Angeles, CA (US); Tsu-Chin Tsao, Manhattan Beach, CA (US); Brittany N. Berry-Pusey, Los Angeles, CA (US); Yen-Chi Chang, Los Angeles, CA (US)

(73) Assignee: THE REGENTS OF THE UNIVERSITY OF CALIFORNIA, Oaklnad, CA (US)

( * ) Notice: Subject to any disclaimer, the term of this patent is extended or adjusted under 35 U.S.C. 154(b) by 146 days.

(21) Appl. No.: 14/347,207

(22) PCT Filed: Sep. 26, 2012

(86) PCT No.: PCT/US2012/057364
§ 371 (c)(1),
(2) Date: Mar. 25, 2014

(87) PCT Pub. No.: WO2013/049228
PCT Pub. Date: Apr. 4, 2013

(65) Prior Publication Data
US 2014/0236045 A1    Aug. 21, 2014

Related U.S. Application Data

(60) Provisional application No. 61/539,335, filed on Sep. 26, 2011.

(51) Int. Cl.
*A61D 7/00* (2006.01)
*A61D 3/00* (2006.01)
(Continued)

(52) U.S. Cl.
CPC ......... *A61B 5/150206* (2013.01); *A01K 15/04* (2013.01); *A61B 17/34* (2013.01);
(Continued)

(58) Field of Classification Search
CPC .......... A61D 1/00; A61D 1/02; A61D 1/025; A61D 7/00; A61B 5/150206; A61B 5/150748; A61B 17/34; A61B 17/3403; A61B 19/22; A61B 19/2203; A61B 19/26; A61B 34/30; A61B 5/0215; A61M 5/427; A61M 5/16854–5/16859; A61M 2005/16863–2005/16872

See application file for complete search history.

(56) References Cited

U.S. PATENT DOCUMENTS 4,709,660 A * 12/1987 Hrushesky ............... A61D 3/00
                                                                    119/751
5,868,678 A *  2/1999 Brunner   .............. A61M 5/1413
                                                                    600/486

(Continued)

FOREIGN PATENT DOCUMENTS

JP      06-036617 U      5/1994
KR   10-2009-0038971      4/2009

(Continued)

OTHER PUBLICATIONS

PCT International Search Report for PCT/US2012/057364, Applicant: The Regents of the University of California, Form PCT/ISA/210 and 220, dated Feb. 25, 2013 (3pages).

(Continued)

*Primary Examiner* — Devin Henson
*Assistant Examiner* — Audrey J Parker
(74) *Attorney, Agent, or Firm* — Vista IP Law Group LLP

(57) ABSTRACT

A system, and a method for its use, provides for placement of a fluid delivery needle into the tail of a laboratory animal. The system includes an animal receiving portion, structure configured to receive, position and restrain a tail of the animal placed in the animal receiving portion and a hollow needle attached to a fluid transfer device. Positioning structure is provided to align the needle and fluid transfer chamber with the restrained tail for proper automated insertion of the needle into a blood vessel within the tail. A lateral actuator operatively connected to the fluid transfer device moves the hollow needle in a forward direction so that it is inserted into the blood vessel of the properly aligned tail. The system can include a computer programmed to automatically perform all of the functions and operate all the components of the system.

11 Claims, 6 Drawing Sheets

(51) Int. Cl.
| | |
|---|---|
| *A61M 5/46* | (2006.01) |
| *A01K 15/04* | (2006.01) |
| *A61B 17/34* | (2006.01) |
| *A61B 5/15* | (2006.01) |
| *A61M 5/32* | (2006.01) |
| *A61M 5/42* | (2006.01) |
| *A61M 5/158* | (2006.01) |

(52) U.S. Cl.
CPC ............... *A61D 3/00* (2013.01); *A61D 7/00* (2013.01); *A61M 5/3287* (2013.01); *A61M 5/427* (2013.01); *A61M 5/46* (2013.01); *A61B 2017/3405* (2013.01); *A61M 2005/1585* (2013.01)

(56) References Cited

U.S. PATENT DOCUMENTS

| | | | | |
|---|---|---|---|---|
| 8,078,256 | B2* | 12/2011 | Zan | A61B 8/0833 219/218 |
| 2002/0111546 | A1* | 8/2002 | Cook | A61B 5/14535 600/322 |
| 2003/0235916 | A1* | 12/2003 | Monahan | C12N 15/88 435/455 |
| 2004/0006309 | A1* | 1/2004 | Rusnak | A61D 1/025 604/131 |
| 2006/0173351 | A1* | 8/2006 | Marcotte | A61B 5/0059 600/473 |
| 2007/0213623 | A1* | 9/2007 | Wekell | A61B 5/0215 600/486 |
| 2010/0274202 | A1* | 10/2010 | Hyde | A61B 5/1405 604/272 |
| 2011/0060229 | A1* | 3/2011 | Hulvershorn | A61B 5/0215 600/486 |
| 2012/0190981 | A1* | 7/2012 | Harris | A61M 5/00 600/439 |
| 2013/0034203 | A1 | 2/2013 | Wang et al. | |

FOREIGN PATENT DOCUMENTS

| | | |
|---|---|---|
| KR | 10-2010-0072873 | 7/2010 |
| WO | WO 2011/028926 | 3/2011 |

OTHER PUBLICATIONS

PCT Written Opinion of the International Search Authority for PCT/US2012/057364, Applicant: The Regents of the University of California, Form PCT/ISA/237, dated Feb. 25, 2013 (3pages).
Li, Tao et al., A Blood Sampling Microsystem For Pharmacokinetic Applications, Design, Fabrication, And Initial Results, Lab Chip. 2009, 9, 3495-3503.
Chen, Xing et al. Microfluidic Chip For Blood Cell Separation And Collection Based On Crossflow Filtration, Sensors and Actuators B 130 (2008), 216-221.
Nakashima, Yuta et al., Blood Plasma Separation And Extraction From A Minute Amount Of Blood Using Dielectrophoretic And Capillary Forces, Sensors and Actuators B 145 (2010) 261-569.
Xie, Fuming et al., Good Preclinical Bioanalytical Chemistry Requires Proper Sampling from Laboratory Animals: Automation of Blood and Microdialysis Sampling Improves the Productivity of LC/MSMS, Analytical Sciences,19(4), 479-485 (2003).
Yang, Sung et al., Device For Continuous, Real Time Blood Plasma Separation, Lab Chip, 6, 871-880 (2006).
Ma, Bo, et al.,Real Time Blood Plasma Separation In A Microfluidic Chip, J Nucl Med. 2009; 50 (Supplemental 2):473; Meeting Abstracts, 50(2) Meeting Abstracts, 473-(May 1, 2009).
Convert,Laurence et al., A New Tool for Molecular Imaging: The Microvolumetric beta Blood Counter, J Nucl Med 2007; 48:1197-1206.
Zivanovic, Aleksandar et al., A Robotic System For Blood Sampling, Information Technology in Biomedicine, IEEE Transactions on Information Technology in Biomedicine, 4(1), Mar. 2000, 8-14.
Paquit, Vincent et al., Near-Infrared Imaging And Structured Light Ranging For Automatic Catheter Insertion, Medium: X, (2006).
PCT International Preliminary Report on Patentability (Chapter I of the Patent Cooperation Treaty) for PCT/JS2012/057364, Applicant: The Regents of the University of California, Form PCT/IB/326 and 373, dated Apr. 1, 2014 (5pages).

* cited by examiner

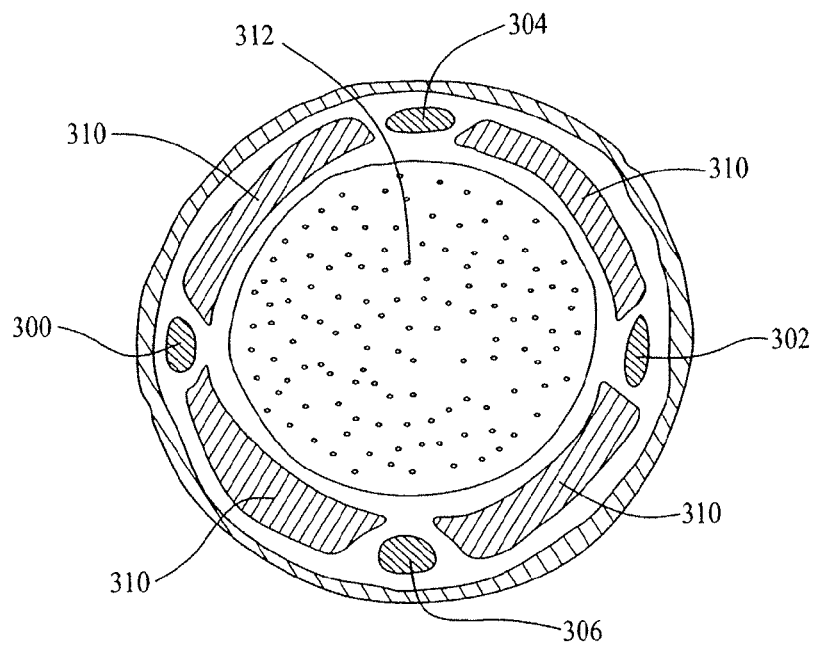
*fig. 4*
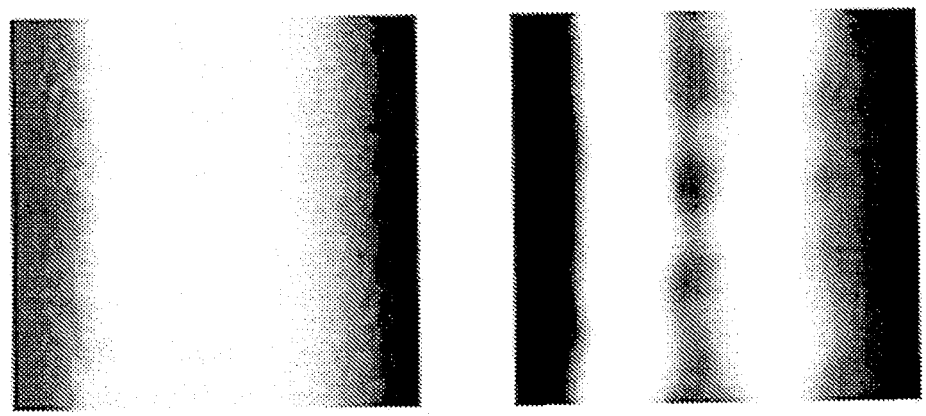
*fig. 5A*          *fig. 5B*

SYSTEM FOR VASCULAR ACCESS IN LABORATORY ANIMALS

CROSS REFERENCE TO RELATED APPLICATIONS

This Application is a U.S. National Stage filing under 35 U.S.C. §371 of International Application No. PCT/US2012/057364, filed Sep. 26, 2012, which also claims priority to U.S. Provisional Application No. 61/539,335 filed on Sep. 26, 2011. The contents of the aforementioned Applications are hereby incorporated herein by reference in their entirely. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH AND DEVELOPMENT

This invention was made with Government support under CA092865, awarded by the National Institutes of Health. The Government has certain rights in the invention.

TECHNICAL FIELD

A system and method is disclosed for accessing tissues and blood vessels in laboratory animals to facilitate injections of fluids into the animal and removal of fluid samples over a period of time.

BACKGROUND

The tail vascular system of a mouse or rat is currently accessed by manually inserting a needle, syringe, or catheter into the lumen of a blood vessel in the tail of the animal by specially trained personnel. Some work has been done on automating the drawing of interstitial fluid of a mouse by creating a mouse "backpack" that arbitrarily pricks the back of a mouse (Li T, Barnett A, Rogers K L, Gianchandani Y B. "A Blood Sampling Microsystem For Pharmacokinetic Applications, *Design, Fabrication, And Initial Results. Lab on a Chip*. (2009)). Work has also been done to automate the blood sampling process after a needle or catheter has been manually inserted into the vascular system (Chen X, Cui D F, Liu C C, Li H., "Microfluidic Chip For Blood Cell Separation And Collection Based On Crossflow Filtration", *Sensors and Actuators B: Chemical.* 130 (1), pp 216-221 (2008); Nakashima Y, Hata S, Yasuda T., "Blood Plasma Separation And Extraction From A Minute Amount Of Blood Using Dielectrophoretic And Capillary Forces," *Sensors and Actuators B: Chemical,* 145(1), pp 561-569 (2009); Xie F, Bruntlett C S, Zhu Y, Kissinger C B, Kissinger P T., "Good Preclinical Bioanalytical Chemistry Requires Proper Sampling from Laboratory Animals: Automation of Blood and Microdialysis Sampling Improves the Productivity of LC/MSMS, *Analytical Sciences,* 19(4), pp 479-485 (2003); Yang S, Undar A, Zahn J D. A Microfluidic "Device For Continuous, Real Time Blood Plasma Separation", *Lab on a Chip,* 6(7), pp 871-880(2006); Ma B, Ghavim S, Sutton R L, Harris N G, Phelps M, Wu H-M., "Real Time Blood Plasma Separation In A Microfluidic Chip", *J Nucl Med Meeting Abstracts,* 50(2) MeetingAbstracts, pp 473—(May 1, 2009); Convert L, Morin-Brassard G, Cadorette J, Archambault Ml, Bentourkia Mh, Lecomte R, "A New Tool for Molecular Imaging: The Microvolumetric beta Blood Counter", *Journal of Nuclear Medicine;* 48(7), pp 1197-1206 (July 2007)). Additionally, work has been done to facilitate inserting needles and catheters in humans. Some of these systems use structured light to locate vessels or probe the skin for vessel location. Once the vessel is located, image guidance or force feedback systems are used for the insertion of the needle. (Zivanovic A, Davies B L. A Robotic System For Blood Sampling. *Information Technology in Biomedicine, IEEE Transactions on,* 4(1), pp 8-14 (2000); Paquit V C, Ferrell T L, Meriaudeau F, et al., Near-Infrared Imaging And Structured Light Ranging For Automatic Catheter Insertion, *Medium: X,* (2006)).

Preclinical molecular imaging technologies have an increasingly broader application base while at the same time are becoming more user friendly. It is believed that no automated or semi-automated system has been developed that allows fluid injections, probe placement and blood sampling from a rodent's tail. Tail vein injections are a routine but critical step in most imaging applications; however, poor injections greatly affect the reliability of experimental results. For at least these reasons, a system and method for readily accessing vessels to facilitate injections and fluid sampling is desired. Embodiments of the invention disclosed herein meet this as well as other needs.

SUMMARY

The system described herein provides the laboratory technician the ability to target specific vessels in a murine preclinical subject (a laboratory animal). In certain embodiments, a near infra-red light can be used to aid in imaging and locating the vessel and micro-needles can be used for injections and/or blood sampling. The laboratory animal is placed in and restrained in a cradle on the system and a needle is inserted using a mechanical system coupled to a feedback system which incorporates pressure sensing as part of the semi close-loop needle placement procedure. The needle can then be integrated with a variety of systems that control the flow of liquids (e.g. microfluidic chip), thereby allowing injections into and blood sampling from the blood stream such as shown in Ma, B, ibid and Convert, L cited above and incorporated herein in their entirety by reference.

In one aspect of the present disclosure, a semi-automated or fully automated vascular access system facilitates injections of fluids into, and blood sampling from, the mouse tail. The handheld needle approach has been replaced by a mechanically directed, remotely controlled, movable needle, incorporating a machine vision system. This approach allows reproducible and repetitive needle placement while reducing the criticality of operator skill in placing the needle, allows the use of significantly smaller needles than those currently used in handheld placement procedures, and has the potential to provide improved control of the time required for needle positioning and the injection of volumes of fluid and the drawing of samples.

In another aspect of the present disclosure, an automated method provided access to the vasculature of preclinical murine subjects for the purposes of direct injection of agents, such as radiopaque dyes or radioactive tracers, into the blood circulation, or for drawing samples of blood during a procedure. Commercial and laboratory applications are numerous; however, in the laboratory environment this system is invaluable for anyone performing experiments with preclinical murine subjects.

In one embodiment, the superficial tail blood vessel is localized using near infra-red imaging and video observation. The tail of the restrained animal is properly positioned and a needle is mechanically aligned with the vessel in the tail in response to the video image. The needle is then inserted into the vessel using a translational actuator. The monitoring and feedback of the needle insertion is accomplished using a pressure transducer connected to the needle. The above mentioned steps can be accomplished either manually or automatically by a computer controlling actuators using the visual and pressure feedback information. Once the needle is inserted, probe injection and/or blood sampling can be accomplished either manually or controlled by microfluidic systems.

Some benefits of using embodiments of this technology, include, for example, improved safety of medical personnel and reproducibility of the needle placement procedure. This is particularly true in cases where infectious agents and other hazardous biological agents are being manipulated, and/or when using laboratory animals that harbor infectious agents.

BRIEF DESCRIPTION OF THE DRAWINGS

Referring now to the drawings in which like reference numbers represent corresponding parts throughout:

FIG. 4 is a schematic drawing illustrating a cross sectional view of a mouse tail.

FIG. 5 illustrates NIR images of a section of a mouse tail where 5a) depicts the original image and 5b) depicts a processed image with the vein in the tail showing as a dark vertical line near the image center.

DETAILED DESCRIPTION

Described below is a preferred embodiment, with reference to the accompanying drawings which form a part hereof, illustrating a specific embodiment and methods for its use. It is to be understood that other embodiments may be utilized, structural changes can be made and additional instrument can be used or certain component can be eliminated without departing from the scope of the present invention.

Positron Emission Tomography (PET) imaging devices for use in preclinical animal studies are becoming more user friendly but to date no system addresses the high skill requirements necessary for injecting labeled compounds for PET visualization (referred to herein as "probe injection") and obtaining blood samples from a preferred site, namely the tail of the mouse. The device described herein provides an automated process for inserting a needle into a mouse tail vessel for fluid and/or probe injections and withdrawal of blood samples.

Besides the high probability of failures in properly setting the needle in the tail vein, poor tail vein injections can greatly affect the quality of radio-images obtained by lowering the probe uptake value as a result of delivering only a small fraction of an intended dose which can occur when a portion of the dose does not enter the tail vein and remains in the surrounding tissue within the tail. In such an instance, the correct input function is unknown, and any standard uptake value (SUV) or calculated kinetic parameters can be inaccurate, because the dose delivered to the subject for the study is not known. Different prior methods to model or measure the input function from images face limitations stemming from the delivery assumptions that are used. Arterial blood sampling from the tail to directly measure the input function is currently not used because of the difficulty of manually accessing the small lumen of the artery in the mouse tail. Instead, arterial blood sampling is often done by accessing the femoral artery. This is performed by using a cut down method and inserting a catheter. However, this requires that the animal be euthanized following the study. Once a reliable and repeatable method is provided to access the tail artery, a simple blood sampling protocol can be achieved without necessitating sacrificing the test animal.

Figure 1:
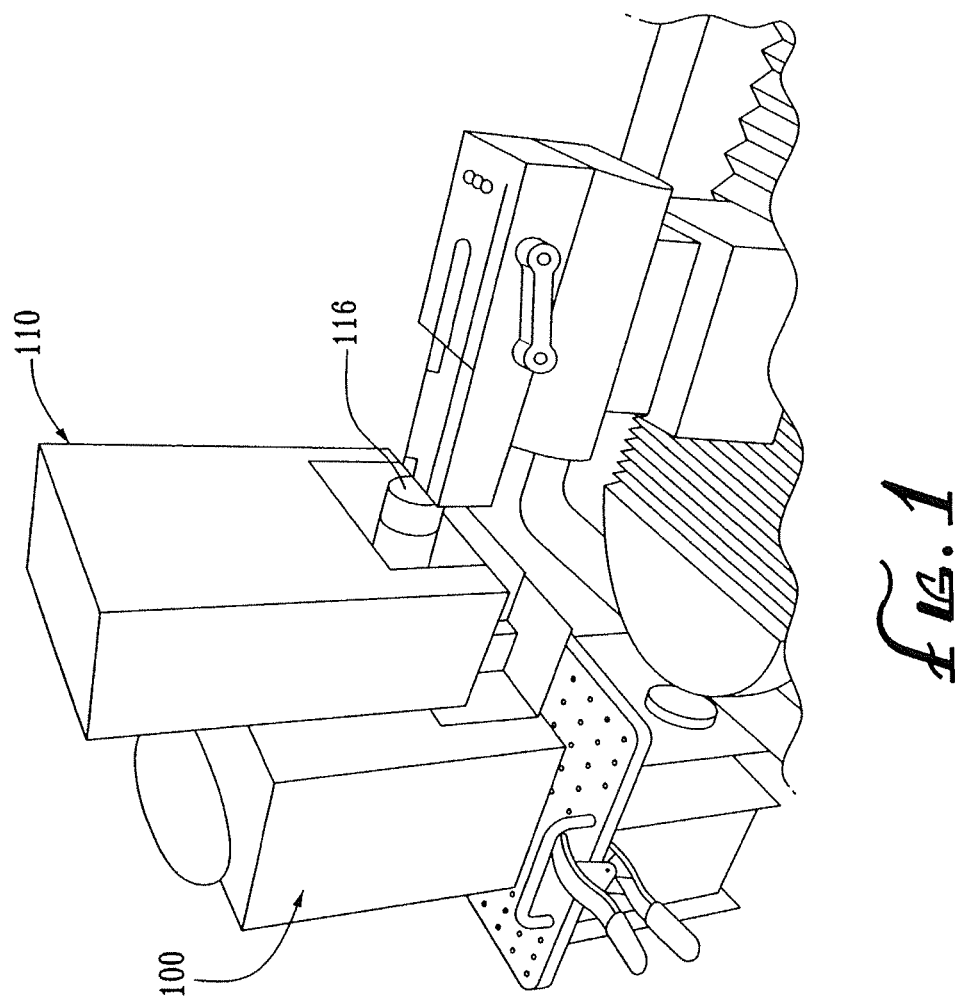
FIG. 1 is a perspective schematic drawing showing an apparatus for use in manipulating small animals for experimental purposes.

FIG. 1 is a schematic representation of a bench-top PET system 100, referred to as the PETbox4, was designed for integrated biological and anatomical preclinical imaging of mouse models. Adjacent the PET system 100 is a mouse atlas registration system (MARS) 110. A laboratory mouse is placed in a cradle 116 for positioning into the bench-top PET system 100 mouse atlas registration system (MARS) 110. This laboratory animal imaging system is more fully described in U.S. patent application Ser. No. 13/564,675 filed 1 Aug. 2012, said application incorporated herein in its entirety by reference. The cradle described below including the mouse subject can be placed in this imaging system once the needle placement in the tail has been accomplished.

Figure 2:
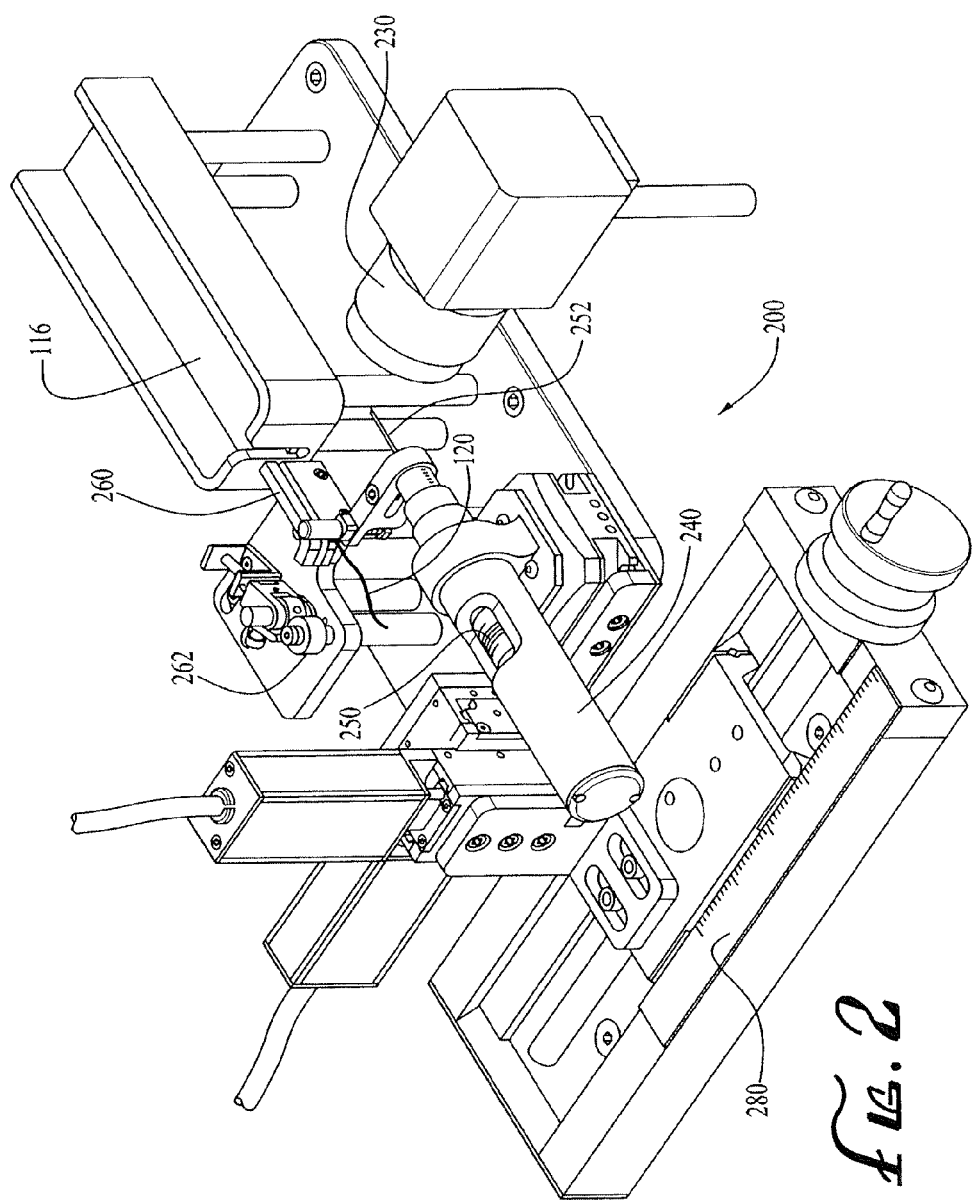
FIG. 2 is a top perspective view of showing a system for injecting a mouse tail incorporating features of the invention.
Figure 3:
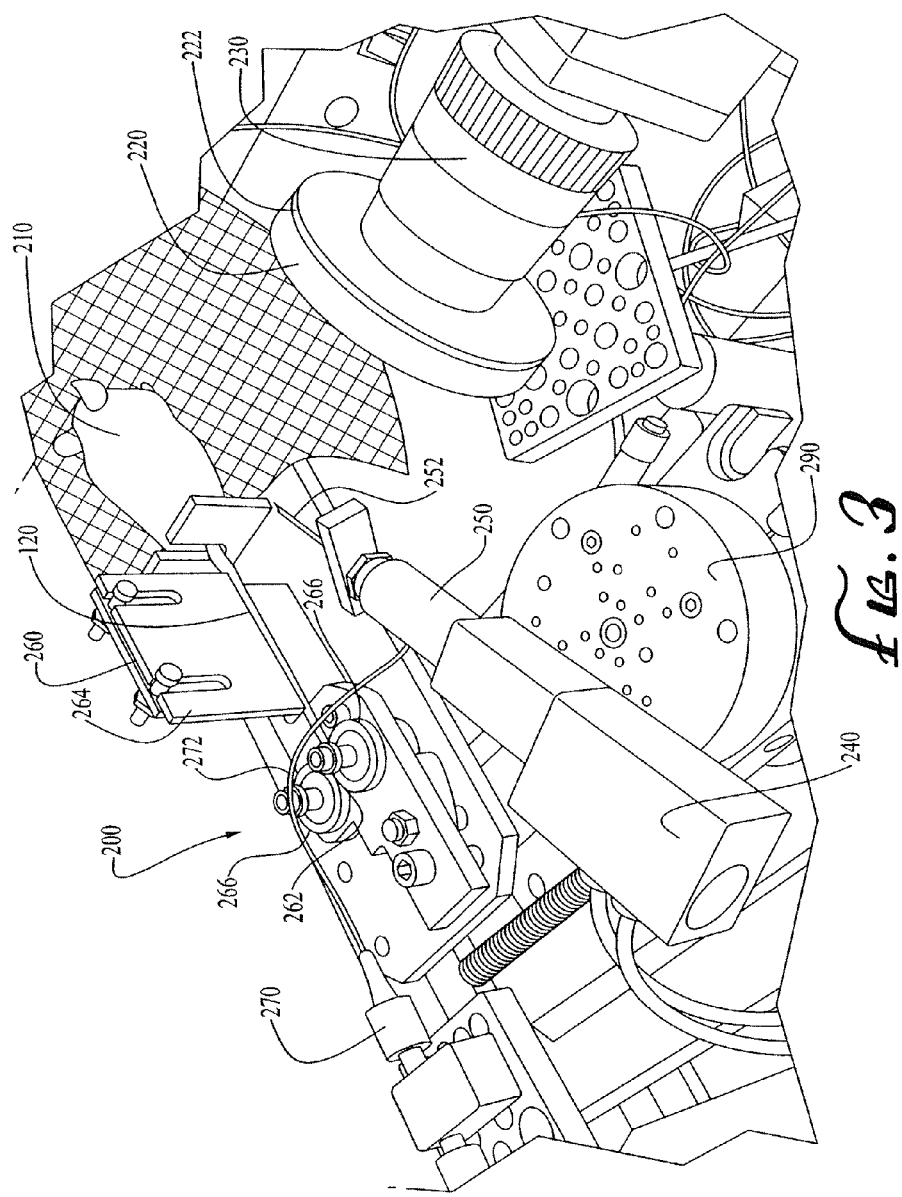
FIG. 3 is an enlarged view of a variation of the system of FIG. 2 including a mouse positioned to receive a needle into the tail.

An embodiment of a laboratory mouse positioning system, mechanical needle placement, fluid delivery and sample recovery system 200 incorporating features of the invention are illustrated by FIGS. 2 and 3. FIG. 2 is a first view of the system 200 while FIG. 3 is an enlarged view of a portion of the system 200, which also shows a laboratory mouse 210 positioned to receive a tail injection which includes a cradle 116 for receiving a mouse 210. The major components of the system are:

a) a light source 220 (shown in FIG. 3 but not in FIG. 2) which can include various lenses, filters, light polarizer 222 and light collimators,
b) one or more cameras 230,
c) a translational actuator 240,
d) a syringe 250 with needle 252,
e) a tail grasping mechanism 260 and a tail tensioner 262,
f) a pressure transducer 270 with pressure transfer tube 272, and
g) a lateral translation mechanism 280.

As best shown in FIG. 3 an anesthetized mouse is positioned within the system, preferably in a cradle 116 with the end of the mouse's tail 120 held in the tail tensioner 262. While FIG. 2 does not show the mouse, it does include a curved line representing the location of the tail 120. The embodiment of the tail tensioner 262 shown in FIG. 3 comprises two adjacent wheels 266, preferably with a non-slip surface, adjustably positioned sufficiently close to each other to grasp the end of the tail 120. The tail is also held in a tail grasping mechanism 260 shown to comprise two parallel plates 264. The syringe 250 with needle 252 is shown in FIG. 2 as being positioned substantially parallel to the tail 120 location. In FIG. 3 the syringe 250 with needle 252 is shown on a rotatable platform 290 repositioned to be at an angle to the orientation of the tail 120. By use of the lateral translation mechanism 280 and the rotatable platform 290 the syringe 250 with needle 252 can be further positioned and the height thereof adjusted so that the needle is substantially in alignment with the tail and at an angle suitable for placement of the needle into the tail. As described herein below, a vein in the tail 120 is located using near IR light and then the translational actuator 240 is activated to move the needle 252 forward to puncture the tail 120 and enter the blood vessel.

FIG. 4 is a schematic cross sectional representation of a mouse tail 120 showing the blood vessels therein which comprise the left and right lateral veins 300, 302, the dorsal vein 304, and the ventral artery 306. Other anatomical features shown are tendon bundles 310 and the coccygeal vertebra 312.

The device described herein, and the automate procedure for its use, eliminates the necessity of using a manual needle placement procedure performed by a highly skilled individual, removing the "art" of tail vein injections and blood sampling as a factor in evaluating the study test results, thus providing a more reproducible and reliable procedure. This apparatus, and the method for its use, provides significant benefits in preclinical PET imaging; however, it can also be utilized in any procedure that requires vascular access in an anesthetized or restrained murine preclinical subject. This includes but is not limited to preclinical SPECT, CT, MRI, optical imaging, drug delivery, drug screening, and cell transfers.

The automated system for injections and blood sampling in preclinical models described and shown herein provides:
Safe and secure tail positioning,
Imaging of the subcutaneous vessel,
The ability to select a wider range of needle sizes,
Image guided movement, by manual or automatic control, and insertion of the needle using mechanical actuators, and
The ability to integrate fluidic control systems (Microfluidic Chip) for fluid sample delivery.

In one aspect of the present disclosure, the superficial blood vessel in the tail is located using near infra-red (NIR) live video imaging. The needle is aligned with the vessel based on the image and manually or through automated mechanical means is then moved forward and inserted into the vessel using a translational actuator. The needle insertion is monitored and feedback is provided by use of a pressure transducer connected to the needle wherein the pressure reading is indicative of whether proper insertion into the blood vessel has been attained. Once the needle is inserted, fluid and/or probe injection and blood sampling can be performed either manually or automatically controlled, for example by use of a microfluidic delivery system.

In the initial step of the process the tail is appropriately tensioned and secured to minimize tail movement during imaging and needle insertion. This is an important step for both anesthetized and unanesthetized mice. The tail is secured in a fashion that does not damage the tail or unnecessarily restrict the blood flow in the vessels. In certain embodiments, a spring loaded multi-wheel clamping system, described below, is used to secure the tail.

In another aspect of the present invention, NIR light and cross polarizers are used to image the tail. In certain embodiments, to localize the vessels, the instrumentation includes one or more CCD cameras or similar image capture devices, an array of NIR LEDs, and two polarizer filters positioned at right angles (cross angle polarizers). An optical IR filter, such as a cast plastic filter, is placed in front of the CCD camera to filter out most of the light with wavelengths shorter than 660 nm. The NIR light is less sensitive than visible light to skin pigmentation and penetrates deeper into the skin, allowing for deeper vessels to be imaged. This overcomes the problems in locating the tail vein, where hairs, pigmentation, and scales located on the surface of the tail may block the visible view.

It is known that cross-polarizers can be used to separate the reflectance of the surface from the light that is backscattered in tissue. There is a change in the refractive index at the air-tissue interface. At this interface, approximately 4% to 7% of the incident light is reflected due to glare at the surface. The remaining portion of incident light enters the tissue and is scattered and/or absorbed. The scattering of the light causes depolarization, yet regular reflectance preserves the plane of polarization. This provides an avenue to minimize the surface reflectance in the mouse tail image. The incident light can be linearly polarized. In one embodiment of the present invention, an analyzing polarizer is used at the CCD. The analyzing polarizer, which is set orthogonal to the polarization of the light, rejects the surface reflected light while allowing some of the scattered light (with random polarization) from the tissue to pass to the CCD. This method of using cross-polarizers enhances the view of the vasculature of the tail. FIG. 5 illustrates NIR images of a section of a mouse tail without (FIG. 5*a*.) and with a polarizing bandpass filter (FIG. 5*b*.). The vein is the dark vertical line near the image center shown in FIG. 5 *b*.

The tail image using the bandpass filter to accentuate the features in the vessel is first obtained. Edge extraction methods are then used to locate the edges of the tail and the edges of the vessel within the tail. The center point between the two vessel edges is then targeted as the needle insertion point.

Besides locating the center of the targeted vessel, an appropriate sized needle can be selected. Decreasing the size of the needle aids in reducing dead volume for blood collection and minimizing vessel damage from the insertion of a needle, and also will allow for wider safety margins in the placement of the needle into the vessel. A preferred needle is a 34 G or 30 G stainless steel beveled tip microneedle which have an outer diameter of 185 and 305 µm, respectively. It has also been verified by analyzing a blood smear from a collected sample that use of this small needle does not damage blood cells when the blood is collected from the tail vein as described herein. Needles of other sizes may be used and in some embodiments, the system can accommodate needles of varying sizes. For example, the system may accommodate and has been successfully tested with both the small 34 G needles and the larger 30 G needles. However, the 30 G or 29 G needles are approximately the same size or slightly larger than the normal tail vein diameter. Therefore, the smaller 34 G needle has the advantage of reducing damage to vessel and provides more leeway in the placement of the needle.

Once the vein has been located, the needle can be inserted. The needle in its carrier is advanced with from 2 to 4 degrees of freedom to attain insertion. Firstly, it is aligned longitudinally with an axis of the vein and is then moved up or down in respect to the tail position. Once the needle is properly aligned, the needle is moved forward by activation of the needle carrier to penetrate the vein. In some embodiments, the needle carrier is controlled manually. In other embodiments, a computer programmed with a fully automated algorithm is used. In one exemplary implementation of the invention, a mechanical stage with four-degrees-of-freedom such as shown in FIGS. 2 and 3, carries the needle and provides the motions required to align and insert the needle into the vessel. In a preferred embodiment a computer controls the needle movement during the insertion process. The needle and needle carrier assembly is configured to rotate around the tail and move up and down relative to the tail for proper alignment and to move the needle forward and back for insertion and removal. Once the needle is properly aligned, it can be inserted using a translational actuator. The translational actuator may be a programmable translational actuator with fine resolution step sizes.

Generally, near-infrared imaging of the tail provides a two dimensional projection and use of additional cameras can help in estimating the depth of the vein. Therefore, while the needle is penetrating into the tissue, there is a need for a feedback signal to indicate when the needle enters the vein and to transmit a signal to the translational actuator to stop forward movement. In one embodiment, the needle is fixed at an acute angle relative to the tail. The needle is inserted in a translational, forward manner until a feedback mechanism indicates the vessel is appropriately penetrated and signals that the forward progression of the needle can be halted. In certain embodiments, the feedback mechanism is a pressure transducer connected by a tube to the proximal end of the needle in a semi-closed loop fashion. The semi-closed loop is filled with a liquid. When an appropriate change in pressure is identified, the actuator stops moving the needle forward. In one embodiment, a pressure transducer is connected to the needle and the transducer and needle are filled with saline. When the needle pierces the vessel wall, a change in pressure occurs and is recorded. This change in pressure provides a signal to the translational actuator to stop forward progression. The needle connection to the pressure transducer can then be switched so that fluid delivery, such as a dose of a radioactive labeled chemical can be delivered.

Figure 6:
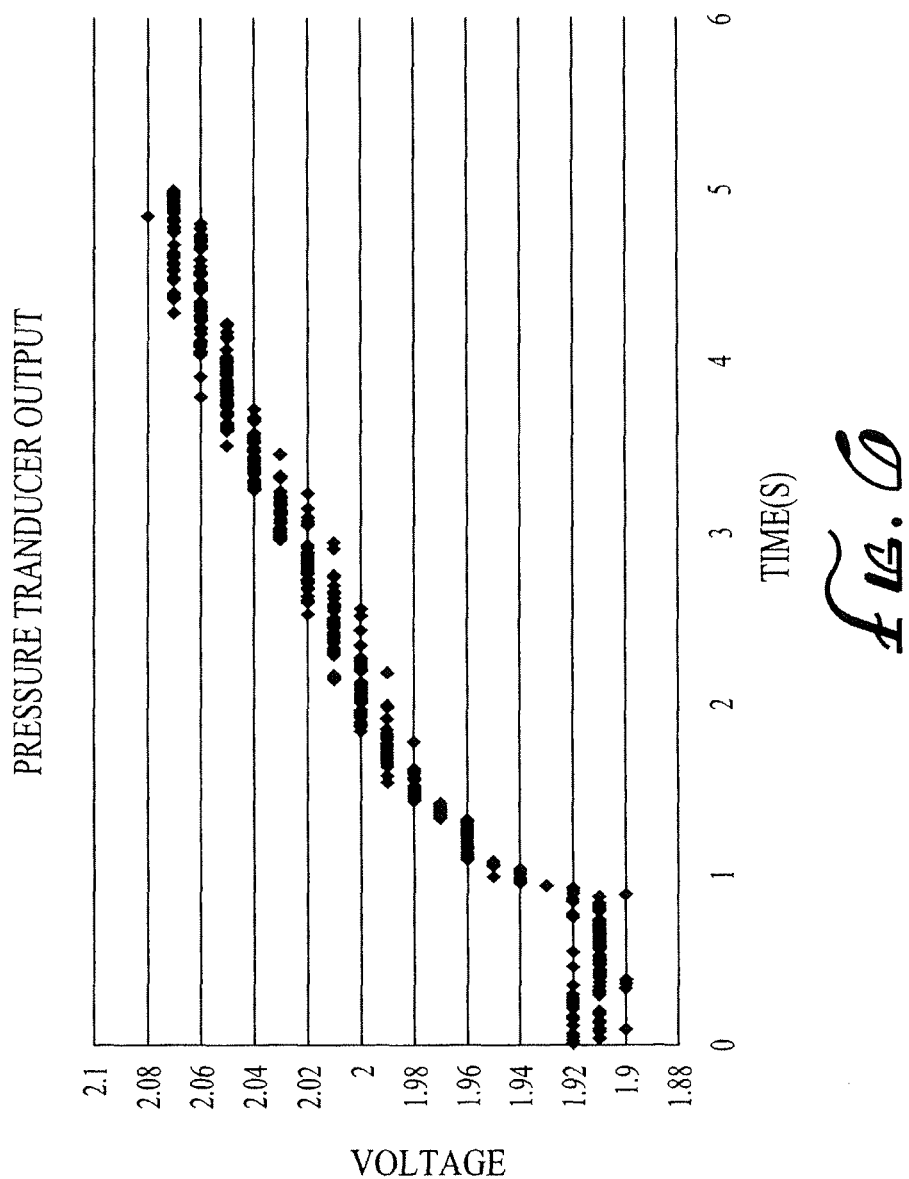
FIG. 6 is a graph illustrating pressure transducer data generated in use of the device as shown in FIGS. 2 and 3.

FIG. 6 is a graph that illustrates the change in pressure, indicate as the transducer voltage output, during a vein puncture using the system described herein. The needle was properly aligned based on the tail image and was inserted into the tail vein using the translational actuator. The change of pressure which occurred at about 1 second signified that the vein was penetrated. The insertion of the needle into the vein was verified by removal of the needle and observation of a drop of blood on the needle tip.

Once the system verifies placement of the needle into a tail vessel fluids or probes can be passed through the needle or blood withdrawn. There are several options to deliver or remove samples, including, but not limited to, manually, with syringe pumps, microfluidic chips or commercialized fluid handling systems such as the VeruTech AccuSampler. By mating a vascular access system described herein to an alternative automated injection and blood sampling device a greater controlled injection and/or blood sampling can occur.

It has been previously shown that microfluidic chips can be used for the synthesis of FDG and whole blood separation. With the development of novel microfluidics based technologies for probe creation, microfluidic chips are becoming more common place in imaging laboratories. The device described herein is an easy platform to transfer the probe from a microfluidic chip into a subject. Additionally, blood sampling greatly benefits from the use of microfluidic chips. The total blood volume of a mouse is usually between 6-8% of its body weight. Therefore, the maximum amount of blood collected at one time should be no greater than 10-15% of the total blood volume or 1% of the mouse body weight. Further, the maximum amount of blood should only be collected once every two weeks so that the blood volume, erythrocytes, and reticulocytes can return to normal levels. Blood sampling protocols are study specific. In general, if whole blood is being analyzed, sample sizes are around 10 ul. If the blood sample must be spun down to analyze the serum, samples typically range from 30-40 ul. For a single one hour dynamic study, around 16 samples are typically withdrawn. Thus, the ability afforded by the system described herein to reduce the amount of blood sampled at each time point and the improved assays that can be run with smaller sample volumes provides more time points for sampling and produces more accurate measurements for use in PET analysis. By mating the automated injection and blood sampling device to a microfluidic chip, more accurate and greater controlled injections and blood sampling can occur.

EXAMPLE 1

Figure 7:
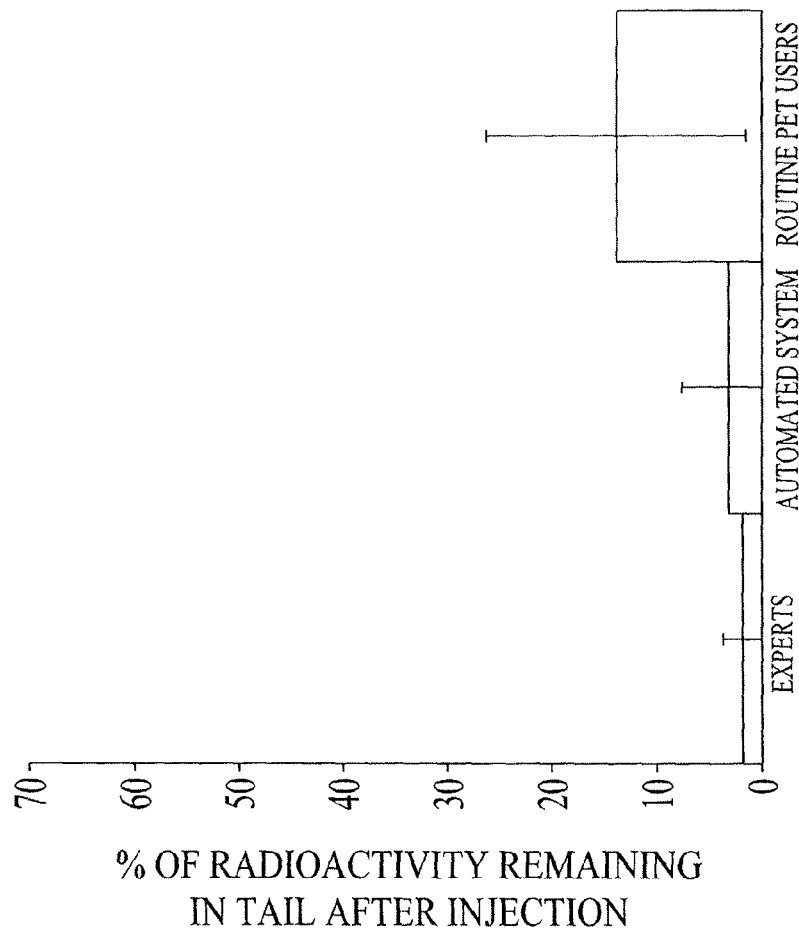
FIG. 7 is a graph illustrating the accuracy of tail vein injections using three different approaches.

The above described device was evaluated for the insertion of a needle into the vein of a mouse tail and the performance of the device was compared to standard manual techniques for injections. After the needle was inserted a syringe was used to inject FDG (a radioactive tracer) through the needle. Quantitative PET imaging was used to analyze the amount of radioactivity left in the tail one hour after the injection. This procedure was performed on 5 different mice. Each mouse was injected after a single attempt of needle insertion with described device. The amount of radioactivity left in the tail was compared to that left in randomly selected studies of injections using manual needle insertions. Because a high skill set is required for tail vein injections, the manual tail vein injectors were separated into two groups. The first group comprised individuals characterized as "expert tail vein injectors." These experts have been performing tail vein injections on a daily basis for several years. The second group of individuals were classified as "routine PET users." Routine PET users were trained to perform tail vein injections and routinely do so, but not on a daily basis. FIG. 7 is a graph illustrating the results of the tail vein injection experiments. A PET image was taken of a mouse 1 hour after being injected with FDG using the mechanical system described above.

The vascular access system was found to reliably locate vessels in the tail of an anesthetized mouse and insert miniature, 34 gauge needles into the vessel using the feedback system to provide information on the success of the needle insertion, which has been verified by PET imaging of the tail. The data shows that the mechanical placement device performs tail vein injections more accurately and consistently than a routine PET user but not as consistently and accurate as placements by "experts". However, because of the reproducibility of the automated system and the safety offered to the operator and other advantages described above, it was found that the automated system provided distinct advantages over prior needle insertion techniques.

A system and method has been disclosed herein for the automated and effective insertion of a needle into the vessels of a mouse or rat tail. The system provides for automated visualization of the animals tail, location of the vein in the tail, using a computer programmed with an appropriate algorithm, properly positioning the needle in relationship to the tail and the vein in the tail, advancing the needle to obtain venipuncture and then, according to preprogrammed protocols, delivering or removing fluids from the tail vein or delivering other materials such as a diagnostic chip to the tail vein. The device aids in preclinical molecular imaging of mice and other mouse handling techniques where access to the mouse tail vessels is necessary. This system also aids the injections to or blood sampling from these animal subjects. While this system was designed to be used in parallel with preclinical PET imaging, it has utility for any work that requires the insertion of a needle into an anesthetized or unanesthetized murine animal.

While the system described herein holds the laboratory animal and the animals tail in a fixed position and moves the needle and related structure for proper alignment with the tail for needle placement, one skilled in the art will recognize, based on the teachings here, and it is so contemplated, that the needle and syringe can be held in a fixed position to be moved forward by the lateral actuator, but the mouse cradle and tail restraining structure can all be on a moveable platform repositionable so that the mouse with restrained tail can be repositioned to properly align with the position of the needle which can then be moved laterally to effect needle insertion.

We claim:

1. A system for placement of a needle into the tail of a laboratory animal comprising:
   a cradle for holding the body of the laboratory animal;
   a tail grasping device comprising two parallel plates and a tail tensioner comprising two spring-biased wheels positioned adjacent to each other and defining a gap for receiving an end of the tail of the laboratory animal, wherein the tail grasping device is located between the cradle and the tail tensioner;
   a light source for illuminating the tail of the laboratory animal with near infra-red light and a camera for imaging the tail of the laboratory animal;
   a needle carrier assembly comprising a rotatable platform holding a syringe with a needle and a lateral translation device coupled to the rotatable platform;
   an automatic translational actuator configured to advance the needle and puncture the tail and enter a blood vessel;
   a pressure transducer connected by a tube to a proximal end of the needle, the needle and tube containing saline therein; and
   a computer programmed to advance the automatic translational actuator and needle, wherein the computer receives a feedback signal from the pressure transducer and stops the automatic translational actuator based on when a pressure measured by the pressure transducer exceeds a preset level or pressure.

2. The system of claim 1, wherein the computer is programmed to advance the needle in fine resolution steps.

3. The system of claim 1, further comprising a cross-polarizing filter interposed in an optical path located between the tail of the laboratory animal and the camera.

4. The system of claim 1, wherein the needle comprises a 34G or 30G needle.

5. The system of claim 1, further comprising an automated fluid delivery device coupled to the needle.

6. The system of claim 5, wherein the automated fluid delivery device comprises a syringe pump or microfluidic chip.

7. A method of placing a needle into a blood vessel within a tail of a laboratory animal comprising:
   placing the laboratory animal on a cradle;
   securing the tail of the laboratory animal in a tail grasping device comprising two parallel plates and a tail tensioner comprising two spring-biased wheels positioned adjacent to each other and defining a gap for receiving an end of the tail of the laboratory animal, wherein the tail grasping device is located between the cradle and the tail tensioner;
   providing a needle carrier assembly comprising a rotatable platform holding a syringe with a needle and a lateral translation device coupled to the rotatable platform;
   providing a pressure transducer that is coupled to the needle via a fluid filled tubing;
   orienting the needle relative to the tail of the laboratory animal using the needle carrier assembly; and
   advancing the needle with an automatic translational actuator to advance the needle and puncture the tail of the laboratory animal and enter a blood vessel, wherein advancement of the needle stops when a pressure measured by the pressure transducer exceeds a preset level or pressure.

8. The method of claim 7, wherein the needle is oriented relative to the tail of the laboratory animal under illumination with near-infrared light.

9. The method of claim 8, wherein light reflected from the tail of the laboratory animal passes through light polarizers.

10. The method of claim 7, further comprising delivering fluids to the laboratory animal via the needle.

11. The method of claim 7, further comprising removing fluids from the laboratory animal via the needle.

* * * * *